United States Patent [19]

Curtis

[11] 4,336,721
[45] Jun. 29, 1982

[54] GAS ANALYZER

[75] Inventor: Richard H. Curtis, Gorham, Me.

[73] Assignee: Hague International, S. Portland, Me.

[21] Appl. No.: 155,940

[22] Filed: Jun. 3, 1980

[51] Int. Cl.³ .............................................. G01N 1/22
[52] U.S. Cl. .............................. 73/863.11; 204/195 S
[58] Field of Search ........................ 73/863.11, 863.12; 204/195 S

[56]  References Cited
U.S. PATENT DOCUMENTS 2,753,246  7/1956  Shields et al. .................... 73/863.11
3,960,500  6/1976  Ross ................................. 73/863.11

Primary Examiner—S. Clement Swisher
Attorney, Agent, or Firm—Wolf, Greenfield & Sacks

[57] ABSTRACT

The gas sampling apparatus may be embodied as a hot sampler or a cold sampler, and basically comprises an insulated housing concentrically supporting an inlet tube which in turn supports a nozzle through which the gas sample is metered, passing to the detection cell. The gas sample is drawn past the cell by an aspirator. A controllable heater is disposed concentrically about the inlet tube and proximate to the aspirator for maintaining the sensing cell at its perferred operating temperature which in one case is 704° C. The aspirator is preferably maintained above 430° C. but below 590° C. by the heater. By maintaining the sample gas in this elevated temperature range, accumulation of residuals of the process are avoided. Provision is made for periodic purging of the apparatus with fresh air to remove residuals from the sampler.

18 Claims, 2 Drawing Figures

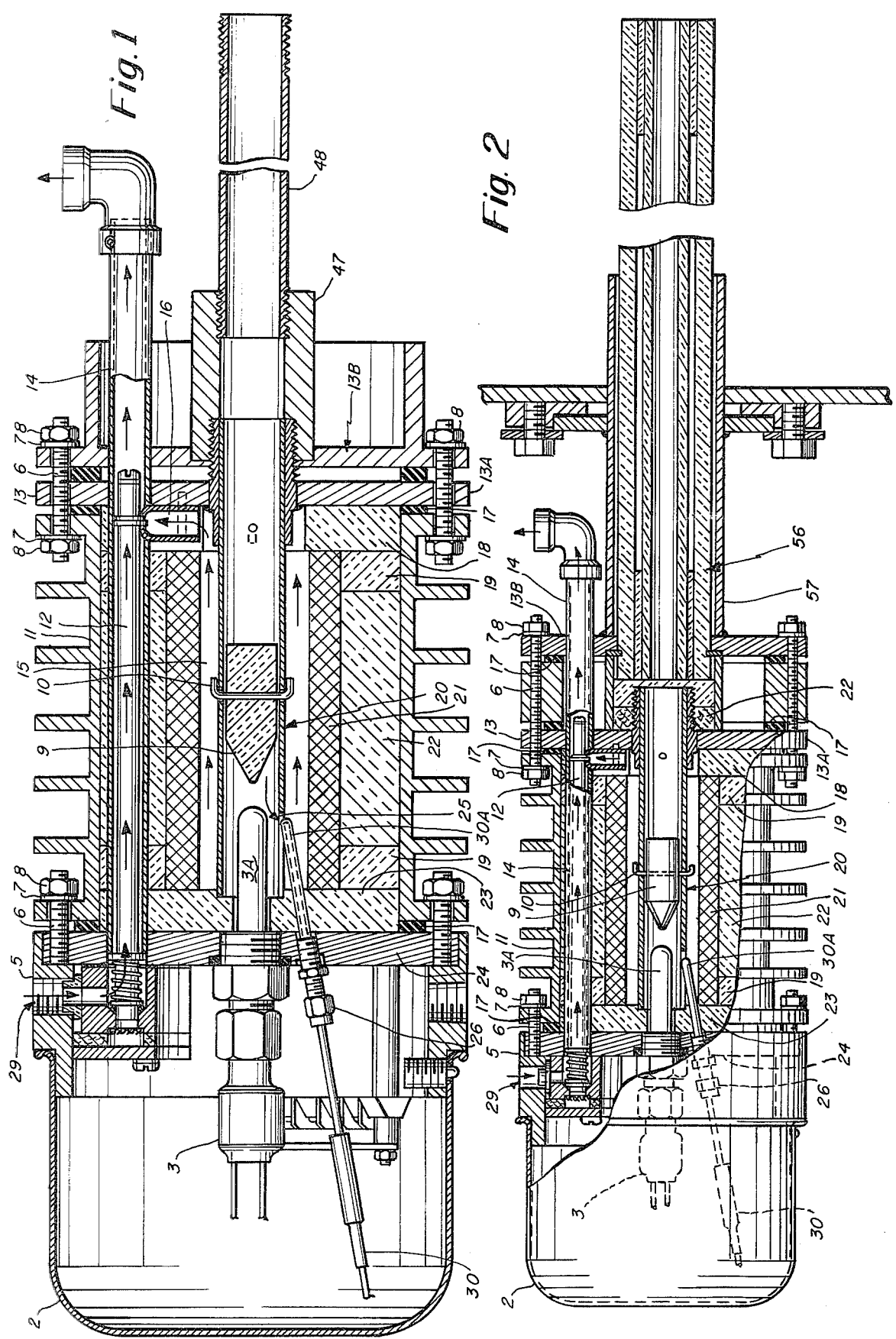

GAS ANALYZER

BACKGROUND OF THE INVENTION

The present invention relates in general to gas sampling apparatus, and more particularly, to an oxygen sensing apparatus and associate system. The embodiments disclosed herein cover both a cold sampler or analyzer and a hot sampler. One of the features of the present invention relates to the self-cleaning aspect with which the sampling occurs.

Many process control and instrumentation systems require that a small sample of gas be extracted from the process for analysis. The analysis may take place in the immediate vicinity of the extraction location, or the gas may be transported considerable distances before the analysis takes place. In practice, problems often arise due to plugging of the system by ash, particulate, water, tar, creosote, carbon, and other residuals of the process. The most severe problems usually occur as a result of the combustion of dirty fuels such as tar, coal, residual oil, wood, or other biomass products. There are usually some residual unburned products either in particulate or vapor form. As these products are drawn into the sampling system, they deposit and/or condense forming a residual deposit which traps other particulates such as ash or dust. These deposits eventually build up and plug the apparatus. These deposits are also often of such a nature that they can not be blown out with an air blast, but must be mechanically removed. Thus, gas sampling systems tend to require high maintenance for most applications with the exception of those involving very clean environments. These systems require periodic cleanout for proper operation. Probably the worst residuals tend to be condensates such as tar and creosote which are not at all easily removed. Such residuals may be those from a combustion process.

Accordingly, one object of the present invention is to overcome the problem of the forming of residual deposits and provide a system that is a self-cleaning system for gas analyzers.

Another object of the present invention is to provide a gas sampling system that requires little maintenance especially in comparison with prior systems and, in particular, those associated with the combustion of dirty fuels. Again, the system of this invention is self-cleaning, thus, drastically reducing the maintenance required.

SUMMARY OF THE INVENTION

To accomplish the foregoing and other objects of this invention, there is provided an apparatus, disclosed herein in the form of both a hot sampler and a cold sampler, for sampling gas wherein the gas sampler is maintained at a sufficiently high temperature so that no condensation of hydrocarbon residues occurs. The apparatus is constructed so that substantially all surfaces that the sample gas contacts maintain this sufficiently high temperature. It has been found in practice that a temperature on the order of 430° C. (806° F.) is sufficient to prevent any accumulation of deposits under a wide variety of fuels and conditions. This temperature is above the boiling point of the highest boiling point organic compound composed of carbon, hydrogen and oxygen: Alizarin ($C_6H_4(CO)_2C_6H_4(OH)_2$). Thus, by maintaining this sufficiently high temperature, there is no possibility of condensation of any organic compound of these elements.

It is of equal importance to prevent the gas sample from being heated to a temperature high enough to cause the entrained ash or particulate to become molten or sticky, in which case it would adhere to the hot surfaces and eventually build up to obscure the passages. The maximum temperature which the sample gas experiences in this case is 704° C. This temperature is sufficiently low to avoid the melting or adhesion of most common combustion residuals.

A still lower temperature, of not over 590° C., will guarantee that even the following compounds:

| | | |
|---|---|---|
| Sodium metavanadate | $N_{a2}O \cdot V_2O_5(Na\ VO_3)$ | 630° C. (1165 F.) |
| Sodium pyrovanadate | $2N_{a2}O \cdot V_2O_5$ | 640° C. (1185 F.) |
| Sodium vanadylvanadate | $N_{a2}O \cdot V_2O_4 \cdot V_2O_5$ | 627° C. (1160 F.) | which are the lowest melting point compounds found as products of combustion of any of the following materials:

gas
oil
residual oil
coal
wood
bark will not become tacky and adhere to the surfaces. It is therefore desirable to avoid temperatures of over 590° C. where possible to avoid problems in even the most adverse instances. In the present case, however, the zirconium oxide sensing cell does not operate properly at a temperature below 704° C., so at least a portion of the gas contacting the cell is heated to that temperature. In principle this could lead to a slagging of the molten ash onto the surface of the cell, although no such problem has arisen in practice.

In accordance with the concepts of this invention, the apparatus is purged with fresh air on a periodic basis. In the event that carbon (soot) has deposited within the apparatus, and has not oxidized due to the low level of oxygen in the sample gas, the carbon is exposed to oxygen at that time, and the high temperature causes oxidation to take place. The product of this oxidation, CO or $CO_2$, is carried away as a gas. The fresh air purge also carries away any ash or particulate which may have accumulated.

In some instances an accumulation of ash will sinter into a solid and adhesive mass even at temperatures as low as 704° C., even though the ash may have been powdery and nonadhesive as it was deposited. This sintering process may take place in as short a time period as one day at 704° C., or appreciably more quickly at higher temperatures. For purposes of keeping the sampler clean it is important to purge it with sufficient frequency to prevent any such solidification of the ash, blowing it out while it is still in a dry and powdery state. In many cases, at a maximum sample temperature of 704° C., a 15 second purge once daily is sufficient to prevent any accumulation of ash in the sampler. The frequency and duration of the purge is dictated by operating considerations and is determined for each different application.

As mentioned previously, the apparatus descried herein is disclosed hereinafter in two different embodiments, one designed for use with a high temperature furnace and the other employing a cold probe for use at temperatures under 593° C. (1100° F.). In either case, the gas sample is drawn from the probe tip past the cell by an aspirator located in the immediate vicinity of the same heater which heats the sensing cell to its operating temperature of, say, 704° C. (1300° F.). The aspirator is maintained preferably above at least 430° C. (806° F.) by this heater.

In accordance with the gas sampling apparatus of this invention, it comprises a housing having means for receiving a sample gas directed into the housing, a gas sensing cell, which may be a zirconium oxide cell, and means supporting this cell in the housing in a position to have the gas sample pass thereover. The gas sample is preferably metered to the gas sensing cell, and in this connection the apparatus may comprise a nozzle or the like disposed in an input tube for passing a metered amount of the gas sample. The apparatus also comprises a heating means which is supported in the housing forming a heated passage both upstream and downstream of the gas sensing cell. Finally, the apparatus comprises a means in the housing for purging the gas sample from the heated passage. A thermocouple is preferably disposed closely adjacent to the cell to sense the temperature in the vicinity thereof. This thermocouple or the like sensing means controls the heater to thus control the temperature in the heated passage. The heater in a sense provides the dual function of maintaining the sensing cell at the proper operating temperature, and at the same time maintaining the aspirator or purging air also at a sufficiently high temperature. In accordance with the present invention, it is preferred that a single heater be employed for both of these functions.

BRIEF DESCRIPTION OF THE DRAWINGS

Numerous other objects, features and advantages of the invention should now become apparent upon a reading of the following detailed description taken in conjunction with the accompanying drawing in which:

FIG. 1 is a cross-sectional longitudinal view showing one embodiment of the present invention as a cold sampler;

FIG. 2 is a cross-sectional longitudinal view showing one embodiment of the present invention as a hot sampler.

DETAILED DESCRIPTION

FIGS. 1 and 2 describe two separate embodiments of the present invention which are preferred constructions, the basic difference therebetween being that the first embodiment is a cold probe or sampler for use at temperatures under, say, 593° C. (1100° F.). The second embodiment is a hot probe or sampler designed for use with high temperature furnaces. The basic construction in both embodiments is quite similar and, thus, like reference characters are applied in both embodiments where appropriate.

Referring now to the two embodiments, each comprises a main cylinder 11 which may be constructed of an aluminum alloy, nozzle inlet tube 20, nozzle 9, cell assembly 3, and aspirator pipe assembly 14. The apparatus comprises a housing which includes at least in part the main cylinder 11 along with face plate assembly 24 at one end, and disc/tube assembly 13 at the other end. The face plate 24 and the disc 13 may be constructed of a metal material whereas many of the component parts of the apparatus are constructed of ceramic.

The end cylinder 5 is also preferably constructed of a metal material and supports the cover 2. The cover protects the oxygen cell assembly 3. The face plate 24 supports the oxygen cell assembly 3. This cell assembly, of course, includes the gas sampling cell 3A. This cell may be a zirconium oxide cell such as one typically sold by Corning Glass. The face plate assembly 24 is preferably secured to the main cylinder 11 by means of a plurality of studs with associated lock washer 7 and hex nut 8. A similar arrangement is used at the other end of the main cylinder 11 employing a stud or bolt along with a lock washer and end nuts. This arrangement secures the other end of the main cylinder to disc/tube assembly 13 which comprises plate 13A and member 13B. In the embodiment of FIG. 1, there is provided a coupling 47 for interconnecting tube 48 and nozzle inlet tube 20. With regard to the disc/tube assembly 13, it is noted that gaskets 17 are provided for sealing the housing in a tight condition.

Within the housing, there are provided a number of thermal insulators for retaining heat internally of the housing. These insulators include an end insulator 18, a ring insulator 19, and insulator 23, and fiber insulation 22.

A heater 21 is disposed about the inlet tube 20 extending between the end insulators 18 and 23. This heater may be a conventional 440 watt heater having electrical input thereto for controlling the heat output thereof. In this regard, there is also provided a thermocouple 30 supported by adapter 26 which is in turn supported in the face plate 24. The adapter supports the thermocouple 30 with the end 30A of the thermocouple disposed closely adjacent to the cell 3A.

The aspirator is actually constructed, or at least the majority thereof, directly within the housing. This aspirator comprises an aspirator tube assembly 12 and an aspirator pipe assembly 14. A fresh air supply (not shown) is coupled to the input port 29. From there, the air passes into the aspirator tube 12 under pressure.

The fresh air passes through the tube 12 out an orifice at its end into the aspirator pipe assembly 14. The jet of air that is thus forced into the pipe 14 sets up a vacuum behind the tube 12. There is, thus, a vacuum in the coupling passage 16 that draws the gas sample from the passage 15 which is defined between the nozzle inlet tube 20 and the inner surface of the heater 21. The inlet tube 20, it is noted, is provided with an opening 25 that permits communication of a gas sample from about the nozzle 9 past the cell 3A and into the upstream passage 15. The aperture 25 also at least in part accommodates a portion of the thermocouple. The vacuum that is established maintains a continuous drawer, as long as the aspirator is operating, for sucking the gas sample into the apparatus.

In the embodiment of FIG. 1, it is noted that the inlet tube 48 is uninsulated. This is the cold sampler embodiment. The sample gas is drawn in through the pipe 48 into the inlet tube 20 and past the nozzle 9. The nozzle meters a predetermined amount of the sample gas thereby passing over the cell 3A and into the heated passage 15. A second purpose of the nozzle 9 is to force the gas into intimate contact with the inlet tube 20, whereby it is heated to the same temperature as the cell, 704° C. in this case. The gas with residual entrained particulate and vapor then escapes through the coupling passage 16 into the aspirator pipe 14 and is exhausted either back into the process gas stream or to the atmosphere depending on the application.

A separate input port adjacent to that labeled 29 is provided for admission of purge air into the aspirator assembly. The passageway is so arranged so that this purge air is forced between the aspirator tube 12 and the pipe 14. When it impinges on the ferrule 4 a large portion is deflected into the coupling passage 16, and then backwards through the system, finally exiting out of the inlet pipe 48. The reverse flushing action of this purge air blast serves to carry away any ash or particulate which may have lodged in the system. This purging of the system is normally carried out on a regular periodic basis, as required.

The embodiment of FIG. 2 is a hot sampler. The construction shown is for the most identical to the construction depicted in FIG. 1, and as indicated previously, like reference characters are applied where appropriate. However, the mounting arrangement is different. This mounting arrangement is not described in detail herein as it does not form an important part of the present invention. The gas sample is drawn through the ceramic intake tube 56 which is supported within the sleeve 57. This intake tube is shown as a two-section tube which may be formed as a composite tube by the use of a ceramic embedding cement.

The gas sample, as with the first embodiment, flows into the inlet tube 20 about the nozzle 9, across the cell 3A and into the downstream heated passage 15. The operation of the apparatus, especially with regard to the cell, heater and aspirator, is substantially identical to the version of FIG. 1. Thus, the thermocouple is used for sensing the temperature in the vicinity of the cell 3A. The output of this thermocouple may then be used to in turn control the electrical current supplied to the heater 21. This operation is for maintaining the cell at its proper operating temperature. As indicated previously, in one example, the heater heats the sensing cell to an operating temperature on the order of 704° C. (1300° F.). The aspirator, including in particular, the aspirator tube 12, is maintained at a somewhat lower temperature but preferably above 430° C. (806° F.).

It is noted that the cylinder 11 is finned. This is provided so as to keep the surface temperature down to a safe level. Although the inlet tube 38 in the first embodiment is of stainless steel some of the other components are preferably of alloys that are more corrosion resistant. For example, the nozle tube 20 may be constructed of a cobalt alloy such as Haynes 188. The nozzle itself is preferably constructed of a high alumina ceramic such as aluminum oxide. Other components such as the cylinder 11 may be constructed of an aluminum alloy.

One of the important features of the present invention is concerned with the aspect of maintaining the cell at a sufficiently high temperature and at the same time maintaining the sample gas as it travels through the apparatus also at a sufficiently high temperature so that no condensation of hydrocarbon residue occurs. Actually, no surface which the gas contacts should be below the minimum predetermined temperature. From experimentation at this time, the minimum temperature should be at least on the order of 430° C. This means that the aspirator in accordance with the invention is also preheated. It is noted that the aspirator tube is disposed closely adjacent to the heater 21 and, thus, as the fresh air is introduced into the aspirator, it is preheated. At the same time, the heater also maintains the sufficient minimum temperature in the area of the nozzle, in the area of the cell itself, and in the passage 15 and couplng passage 16.

Also, in accordance with the present invention, there is provided a method of gas sampling wherein the method is practiced primarily by maintaining a sufficiently high temperature both in the vicinity of the cell and preferably upstream and downstream of the cell. In accordance with this method, the sample is metered prior to passing by the cell and the sample is thereafter maintained at an elevated temperature to prevent the deposit of residuals including even the maintaining of the aspirator air at elevated temperature.

What is claimed is:

1. Gas sampling apparatus comprising;
   a housing,
   an inlet tube means for receiving a sample of gas and supported within said housing,
   a gas sensing cell,
   means disposing the gas sensing cell in the housing in a position to have the gas sample pass thereover,
   a heating means,
   means supporting the heating means in the housing about at least a section of the inlet tube means and forming a heated gas passage disposed about the inlet tube means,
   means providing gas communication from the inlet tube means to the gas passage,
   nozzle means,
   means supporting the nozzle means in the inlet tube means in a position to block a portion of the inlet tube and meter the gas flow, and
   aspirator means at least in part in the housing for purging the gas sample from the heated passage.

2. Gas sampling apparatus as set forth in claim 1 including means for sensing the temperature in the heated passage to control the heating means.

3. Gas sampling apparatus as set forth in claim 2 wherein said means for sensing includes thermocouple means disposed adjacent said gas sensing cell.

4. Gas sampling apparatus as set forth in claim 1 including means in the housing associated with the means for receiving the sample for metering flow to the gas sensing cell, wherein said means for metering includes nozzle means and said means for receiving the sample includes an input tube having the nozzle means supported therein, and, wherein said cell is disposed concentrically relative to said nozzle means and input tube.

5. Gas sampling apparatus as set forth in claim 1 wherein said heating means is coaxially arranged in the housing extending from said gas sampling cell to the aspirator means and defining on the interior thereof at least part of the heated passage.

6. Gas sampling apparatus as set forth in claim 1 wherein said aspirator means includes an aspirator tube extending longitudinally of the housing on the outside of but adjacent said heating means.

7. Gas sampling apparatus as set forth in claim 1 wherein said heating means is disposed so as to also heat the aspirator air.

8. Gas sampling apparatus as set forth in claim 1 wherein said heating means maintains the cell at a temperature on the order of 704° C.

9. Gas sampling apparatus as set forth in claim 1 wherein said aspirator air for purging the sample is preheated to at least a minumum temperature on the order of 430° C.

10. A method of sampling a gas for analysis thereof including a gas sensing cell disposed within a housing having a gas passage, comprising the steps of; maintaining the gas passage in the vicinity of the cell at at least a minimum temperature on the order of 430° C. greater than a minimum temperature that prevents water condensation and sufficiently high to prevent formation of hydrocarbon residuals, passing the gas sample over the gas sensing cell, maintaining the temperature of the gas sample at the gas sensing cell greater than said minimum temperature on the order of 430° C., maintaining the gas sample of at least said minimum temperature after passing said cell, and aspiring the gas sample by means of a preheated fresh air also of at least said minimum temperature.

11. A gas sampling apparatus as set forth in claim 1 wherein the sample gas is on the one hand heated to and kept above a minimum temperature on the order of 430° C., but on the other hand is not allowed to exceed a maximum temperature on the order of 704° C.

12. A method of sampling gas as set forth in claim 11 including maintaining the cell temperature on the order of 704° C. and the sample gas temperature of a minimum of at least 430° C.

13. A method as set forth in claim 10 including maintaining said minimum temperature in a range of 430° C. to 704° C.

14. A method as set forth in claim 10 including maintaining the cell temperature on the order of 704° C. and the sample gas temperature within the housing at a temperature of at least 430° C.

15. Gas sampling apparatus as set forth in claim 1 wherein said nozzle means comprises a plug nozzle providing an annular restricted orifice defined between the nozzle and inlet tube means, said nozzle directing the incoming gas sample against the inner surface of the inlet tube means to preheat the gas sample to a temperature sufficient to permit gas detection and greater than 430° C.

16. Gas sampling apparatus as set forth in claim 15 wherein said gas sensing cell is disposed at least in part in the inlet tube means adjacent said nozzle.

17. Gas sampling apparatus as set forth in claim 16 wherein said means providing gas communication comprises an aperture in the inlet tube means.

18. Gas sampling apparatus as set forth in claim 1 wherein said gas sampling occurs absent the necessity of filtering.

* * * * *